(12) United States Patent
Skaper et al.

(10) Patent No.: US 9,498,577 B2
(45) Date of Patent: Nov. 22, 2016

(54) DOSING SYSTEM

(71) Applicant: Raumedic AG, Helmbrechts (DE)

(72) Inventors: Frank Skaper, Leupoldsgrün (DE); Gero Eichelkraut, Dresden (DE); Thomas Braun, Hof (DE); Bernd Spindler, Helmbrechts (DE); Dirk Witzel, Eichenzell (DE); Mirko Krimmel, Hünfeld (DE); Andreas Vogt, Geisa (DE)

(73) Assignee: Raumedic AG, Münchberg (DE)

( * ) Notice: Subject to any disclaimer, the term of this patent is extended or adjusted under 35 U.S.C. 154(b) by 214 days.

(21) Appl. No.: 14/271,889

(22) Filed: May 7, 2014

(65) Prior Publication Data

US 2014/0336591 A1    Nov. 13, 2014

(30) Foreign Application Priority Data

May 7, 2013 (DE) .................. 10 2013 208 390

(51) Int. Cl.
*A61M 5/315* (2006.01)

(52) U.S. Cl.
CPC ....... *A61M 5/31543* (2013.01); *A61M 5/3156* (2013.01); *A61M 5/31555* (2013.01); *A61M 5/31563* (2013.01); *A61M 2005/31508* (2013.01)

(58) Field of Classification Search
CPC ..................... A61M 5/31543; A61M 5/3156; A61M 5/31563; A61M 5/31555; A61M 2005/31508
See application file for complete search history.

(56) References Cited

U.S. PATENT DOCUMENTS

| 5,183,466 A | 2/1993 | Movern |
| 2012/0316509 A1 | 12/2012 | Kayser et al. |

FOREIGN PATENT DOCUMENTS

| DE | 355 945 | 7/1922 | |
| DE | 1 035 858 | 8/1958 | |
| EP | 1 459 776 | 9/2004 | |
| EP | 2 570 145 | 3/2013 | |
| FR | WO 2013037937 A1 * | 3/2013 | ........ A61M 5/31555 |

OTHER PUBLICATIONS

EP Search Report, dated Aug. 14, 2014, from corresponding EP application.

* cited by examiner

*Primary Examiner* — Kevin C Sirmons
*Assistant Examiner* — Amber Stiles
(74) *Attorney, Agent, or Firm* — Boyle Fredrickson S.C.

(57) ABSTRACT

The invention concerns a dosing system for adjusting a dose volume of a fluid medium. The dosing system has a longitudinal center axis, a dosing sleeve with at least one communication opening, a dosing plunger, which can move axially in the dosing sleeve between a retracted and a depressed position to take up and dispense the medium through the communication opening, and a retraction limiting element to delimit a maximum axial retraction path of the dosing plunger. The retraction limiting element in at least one position can be axially fixed to the dosing plunger and can move radially to the longitudinal center axis between an inner position, axially fixed on the dosing plunger, and an outer position relative to the dosing plunger. In the inner position, it is completely inside the dosing sleeve. Furthermore, the dosing system has an end stop arranged on the dosing sleeve for interaction with the retraction limiting element in the retracted position of the dosing plunger.

20 Claims, 5 Drawing Sheets

DOSING SYSTEM

CROSS-REFERENCE TO RELATED APPLICATIONS

This application claims the priority of German patent application, Serial No. DE 10 2013 208 390.4, filed May 7, 2013, pursuant to 35 U.S.C. 119(a)-(d), the content of which is incorporated herein by reference in its entirety as if fully set forth herein.

FIELD OF THE INVENTION

The invention concerns a dosing system for adjusting a dosage volume of a fluid medium, such as a liquid medication.

BACKGROUND OF THE INVENTION

Dosing systems whose dosage volumes are adjustable are known from the prior art. These dosing systems generally comprise a dosing sleeve and a dosing plunger that is moved in translation in the dosing sleeve. To adjust the particular dosage volume, external stop elements are arranged on the dosing plungers along the periphery in the desired dosing position and extend through to the outside by a corresponding window in the dosing sleeve. The drawback to these known dosing systems is that their manipulation is often not user-friendly. Moreover, the handling is not always intuitive.

DE 355 954 B describes a syringe for medical purposes. DE 1 035 858 A and U.S. Pat. No. 5,183,466 describe various designs of an injection syringe.

SUMMARY OF THE INVENTION

Therefore, the problem of the invention is to provide a dosing system for adjusting a dosage volume of a fluid medium which is extremely user-friendly and intuitive. Moreover, the dosing system should be protected against manipulation and simple to manufacture.

This problem is solved according to the invention by the features indicated in claim 1. The crux of the invention lies in the fact that the retraction limiting element is arranged entirely in its inner position or in its totality inside the dosing sleeve. Since the retraction limiting element is situated entirely inside the dosing sleeve in its inner position, an inadvertent manipulation of the retraction limiting element or the retraction process is made difficult or impossible. The retraction limiting element is protected by the dosing sleeve in its inner position. The dosing plunger can be moved relative to the dosing sleeve when the retraction limiting element is in its inner position. The dosing plunger can also move relative to the dosing sleeve when the retraction limiting element is in its outer position.

The dosing system is used preferably in pediatric medicine or in the treatment of the elderly.

As already mentioned, the retraction limiting element in its inner position is arranged entirely within the dosing sleeve. Even so, the dosing sleeve can have at least one peripheral opening, aperture, window or the like, which has no influence on this treatment of the entirely inner arrangement. The retraction limiting element is arranged in the inner position in the receiving space of the dosing sleeve.

The dosing sleeve bounds a receiving space for the medium being dispensed on the outside. The at least one communicating opening allows the medium to enter the receiving space. Moreover, the medium situated in the receiving space can be dispensed again from the receiving space through the at least one communication opening.

In the retracted position of the dosing plunger the receiving space is at maximum volume, while in the depressed position of the dosing plunger it is at its minimum.

It is advantageous for the retraction limiting element to be able to move between its positions perpendicular to the longitudinal center axis. Alternatively, a slanting or rotational displacement relative to the longitudinal center axis is possible.

In the retracted position of the dosing plunger, the retraction limiting element located in the inner position strikes against the end stop and thus together with the end stop limits the dosing volume. The retraction limiting element thus forms an abutment for the end stop, which thus forms a kind of dosing stop. Thanks to the tactile and mechanical end stop, in contrast with purely visual settings, an overdose is impossible. With traditional dosing syringes, wrong doses occur on average at 35% of the dosing quantity, while with traditional dosing spoons wrong doses occur on average at 85% of the dosing quantity. Thus, the tactile stop leads to increased safety, which is especially advantageous for highly active medications and low dose volumes. Even visually impaired persons can thus adjust or perform an accurate dosing.

The retraction limiting, element is advantageously axially adjustable in at least two different positions, separated from each other in the direction of the longitudinal center axis. Preferably, the retraction limiting element is axially adjustable in at least five, preferably at least ten, preferably at least fifteen different positions on the dosing plunger that are separated from each other in the direction of the longitudinal center axis. Thanks to this configuration, an extremely fine dose incrementation with many dose increments is created. Since the retraction limiting element is axially adjustable on the inner dosing plunger, there is an internal dose incrementation, which leads to a compact design of the dosing system.

Moreover, essentially the entire retraction path or lifting path is available in the dosing system for the dosing of the medium being dispensed. In particular, the lifting path is not occupied or reduced by an end stop.

The retraction limiting element is preferably clamp-like. It is advisable for the retraction limiting element to be symmetrical, preferably U-shaped.

It is advantageous to provide a lose scale on the dosing sleeve.

Advisedly, the dosing system is designed as a syringe. The design is preferably oriented to known dosing syringes which patients are customarily using. Preferably the dosing system is extremely compact in design.

It is advantageous for the dosing system to not have any loose parts. The parts of the dosing system are thus captive.

It is advantageous for the retraction limiting element to have an activating head for the manual movement of the retraction limiting element between the outer position and the inner position. The activating head enables an easy and safe displacement of the retraction limiting element between the outer position and the inner position, preferably from the outer position to the inner position. Especially preferably, the movement is reversible or alternatively irreversible from the outer position to the inner position.

The dosing system is extremely cheap and easy to produce.

Further advantageous embodiments of the invention are given in the subclaims.

According to claim 2 a maximum transverse dimension of the retraction limiting element is smaller than the inner diameter of the dosing sleeve. All dimensions of the retraction limiting element perpendicular to the longitudinal center axis are thus smaller than the inner diameter of the dosing sleeve, or more accurately, than the inner diameter of the main cylinder of the dosing sleeve.

The configuration of claim 3 enables a secure and simple axial fixation of the retraction limiting element on the dosing plunger. A radial fixation is additionally possible by a form-fitting connection between the retraction limiting element and the dosing plunger. Instead of a locking connection, a plug connection is also possible, for example. The form-fitting connection in the inner position of the retraction limiting element can be one time or repeatedly locking or releasing, winch enables a disassembly of the dosing plunger from the dosing sleeve or a removal of the dosing plunger from the dosing sleeve. Such a disassembly or removal is advantageous, for example, for cleaning purposes.

According to claim 4, the first form fitting means are arranged in a strip of form fitting means. The first form fitting means are preferably provided on the outside of the dosing plunger. If is advantageous for the second form fitting means to be arranged on the inside of the retraction limiting element. The first and second form fitting means are complementary to each other in configuration. Preferably, a locking or plug connection is provided between the form fitting means.

The configuration according to claim 5 prevents an unintentional manipulation of the dosing system and thus an unintentional changing of the dose volume. It is advantageous for the retraction limiting element in the inner position to be axially secured both axially and also perpendicularly to the longitudinal center axis. As already mentioned, however, a releasable connection between the retraction limiting element in the inner position and the dosing plunger is also possible as an alternative, which is advantageous for cleaning purposes, for example.

Preferably, at least one locking element is arranged on the dosing plunger and extending in the direction of the longitudinal center axis. More preferably, several first locking elements are arranged on the dosing plunger, being spaced apart from each other in the direction of the longitudinal center axis. Advisedly, at least one first locking abutment is arranged on the retraction limiting element, which is interlocking with at least one of the first locking elements in the inner position of the retraction limiting element and impedes or prevents a radial movement of the retraction limiting element outward from the longitudinal center axis.

Preferably, at least one second locking element is arranged on the dosing plunger and extending in the direction of the longitudinal center axis. More preferably, several second locking elements are arranged on the dosing plunger and spaced apart from each other in the direction of the longitudinal center axis. Advisedly, at least one second locking abutment is arranged on the retraction limiting element, which is interlocking with at least one of the second locking elements in the inner position of the retraction limiting element and impedes or prevents a radial movement of the retraction limiting element outward from the longitudinal center axis.

When the retraction limiting element is in its inner position, the retraction limiting element engages with the dosing plunger, preferably by a locking, which prevents an outward radial movement of the retraction limiting element. This inner position of the retraction limiting element forms a dosing position. The retraction limiting element is then axially fixed on the dosing plunger.

It is advantageous for the retraction limiting element to also engage by locking with the dosing plunger in its outer position. This locking engagement also enables a movement of the dosing plunger in the direction of the longitudinal center axis relative to the retraction limiting element. The engagement is releasable.

The feedback according to claim 6 can be tactile and/or acoustical, for example. Preferably several feedback recesses or interruptions are provided on the dosing plunger, being arranged at a spacing from each other in the direction of the longitudinal center axis. Upon axial displacement of the dosing plunger relative to the retraction limiting element, there is preferably a releasable engagement between the at least one first and/or second locking abutment and the recesses or interruptions. The retraction limiting element thus rattles preferably on the dosing plunger during a relative displacement movement between the dosing plunger and the retraction limiting element. Thus, the finding of the first form fitting means is preferably acoustically and tactilely supported. The rattling thus advisedly provides the user with a tactile and/or acoustical feedback. This outer position of the retraction limiting element constitutes an installation position.

The activation window of claim 7 enables an easy and safe displacement of the retraction limiting element relative to the dosing plunger.

In the embodiment of claim 8, the retraction limiting element forms a bar and thus limits or prevents a relative movement between the retraction limiting element and the dosing sleeve in the direction of the longitudinal center axis. The retraction limiting element is essentially flush on the outside with the dosing sleeve or its main cylinder. This leads to an extremely robust dosing system. In particular, this prevents in easy manner the retraction limiting element from being moved unintentionally into its inner position, which would result in an unintentional setting of a dose volume.

In the embodiment of claim 9, a relative movement between the retraction limiting element and the dosing sleeve in the direction of the longitudinal center axis is essentially prevented.

The embodiment of claim 12 leads to a dosing system which is extremely user-friendly. Thus, the end stop can be easily fixed in place when on the dosing sleeve as the installation proceeds. The end stop can be arranged directly or indirectly on the dosing sleeve. A one piece configuration with the dosing sleeve is alternatively possible. It is advantageous for the end stop to be locally fixed by at least one snap hook to the dosing sleeve.

The dosing system per claim 13 enables an especially large change in the adjustable dose volume.

The configuration per claim 14 results in an extremely simple adjustment of the desired dose volume.

The embodiment of claim 15 forms a kind of captive arrangement. The retraction limiting element is captively secured to the dosing plunger. Thus, it cannot get lost.

It is advantageous for the dosing system to be provided or delivered when the retraction limiting element is in its outer position or installation position. It is then easily possible for a doctor, a pharmacist, or the like, to specify a dose quantity.

In combination with the preceding claims or features, but also as an independent invention, the dosing plunger has at its first end a displacement body projecting in the direction of the longitudinal center axis to penetrate or insert into the at least one communication opening and in its piston bottom at least one depression running around the displacement body, and at least elevation which is complementary to the at least one depression is formed in a bottom of the dosing sleeve, while preferably the dosing plunger comprises at least one drainage groove on its piston bottom and the displacement body to improve the residual emptying. The at least one drainage groove delimits a drainage channel for the fluid medication and enables an especially good flowing and an especially thorough residual emptying of the fluid medium being dispensed. Moreover, a very exact dosing of the fluid medium is possible in this way.

Advisedly, the at least one depression and the at least one elevation engage with one another when the dosing plunger is in its fully depressed position. The depression(s) and the elevation(s) preferably run in a ring around the longitudinal center axis.

The at least one drainage groove has an angular or a circular arc-shaped cross section, for example.

It is advantageous for the at least one drainage groove to have a depth that is between 0.05 mm and 0.4 mm, more preferably between 0.1 mm and 0.25 mm.

Advisedly, the at least one drainage groove has a width that is between 0.4 mm and 1.2 mm, more preferably between 0.6 mm and 1.0 mm.

In the area of the piston bottom, the at least one drainage groove extends basically radially to the longitudinal center axis, while in the area of the displacement body it extends basically parallel to the longitudinal center axis. Advisedly, each drainage groove extends along its length in a plane in which the longitudinal center axis is also preferably situated.

If several drainage grooves are present, these advisedly have an identical angular spacing from each other.

It is advantageous for the at least one drainage groove in the piston bottom to broaden radially outward, starting from the longitudinal center axis, more preferably to broaden essentially continuously radially outward.

BRIEF DESCRIPTION OF THE DRAWINGS

In what follows, a preferred embodiment of the invention shall be described as an example, making reference to the enclosed drawing. There are shown.

DETAILED DESCRIPTION OF THE PREFERRED EMBODIMENTS

Figure 1:
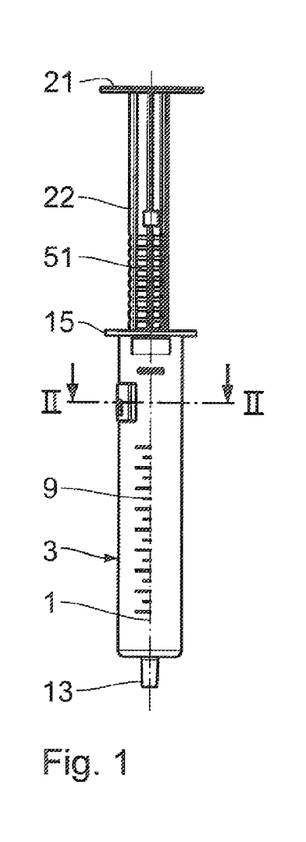
FIG. 1: a side view of a dosing system according to the invention, in which the retraction limiting element is situated in its outer position.
Figure 2:
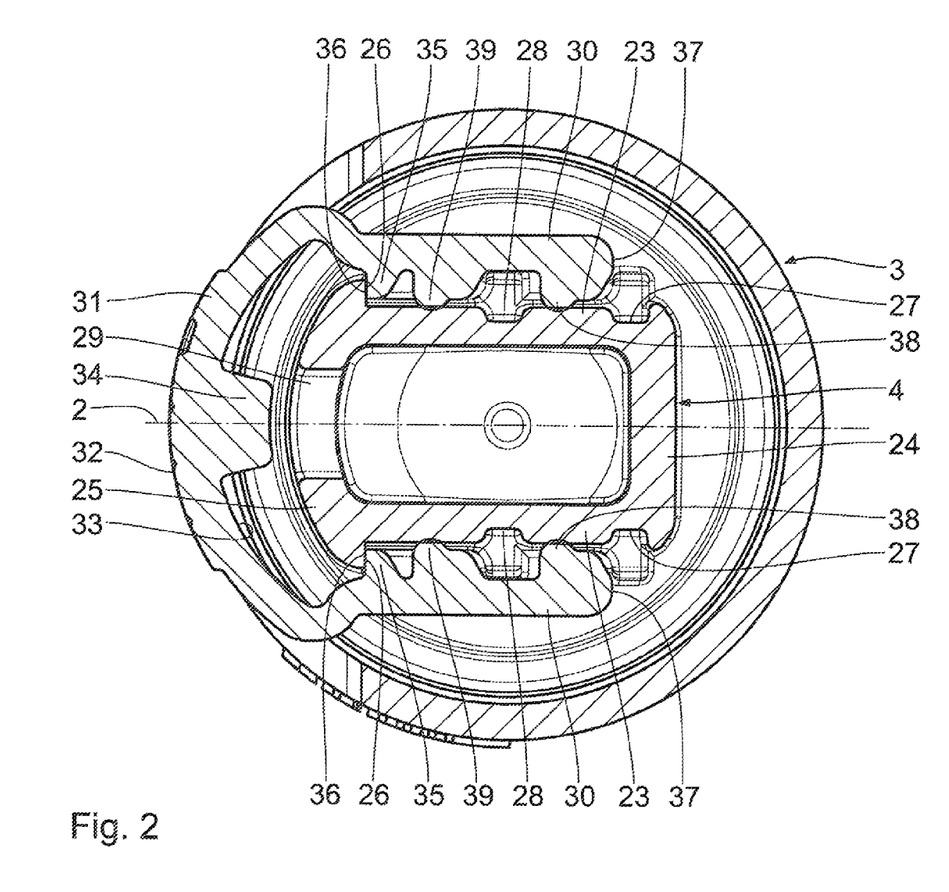
FIG. 2: a cross section through the dosing system according to the invention along the line II-II in FIG. 1, FIG. 3: a side view of the dosing system according to the invention per FIG. 1, wherein the retraction limiting element is situated in its inner position.
Figure 3:
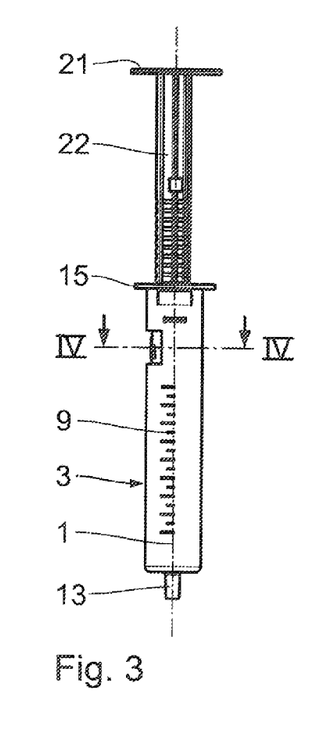
Figure 4:
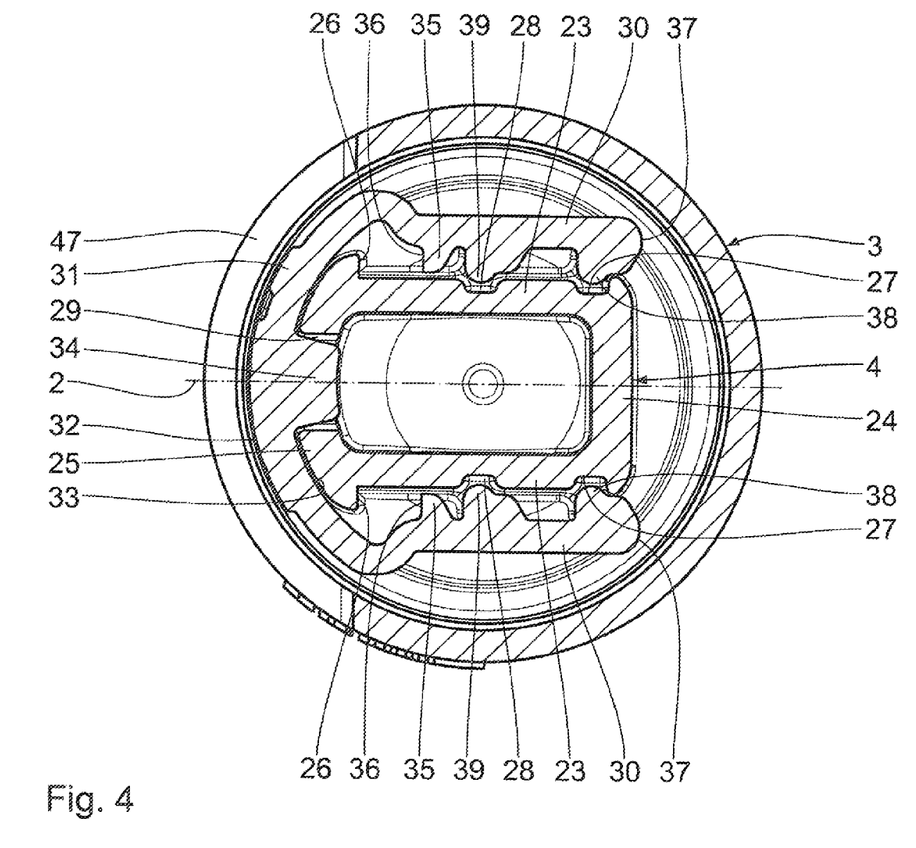
FIG. 4: a cross section through the dosing system according to the invention along the line IV-IV in FIG. 3, FIG. 5: a first longitudinal section through the dosing system according to the invention shown in FIG. 1 to 4, FIG. 6: a second longitudinal section through the dosing system according to the invention shown FIGS. 1 to 5, the longitudinal section being tilted about the longitudinal center axis as compared to FIG. 5, and FIG. 7: a view showing the dosing system illustrated in FIG. 1 to 6, from the bottom.
Figure 5:
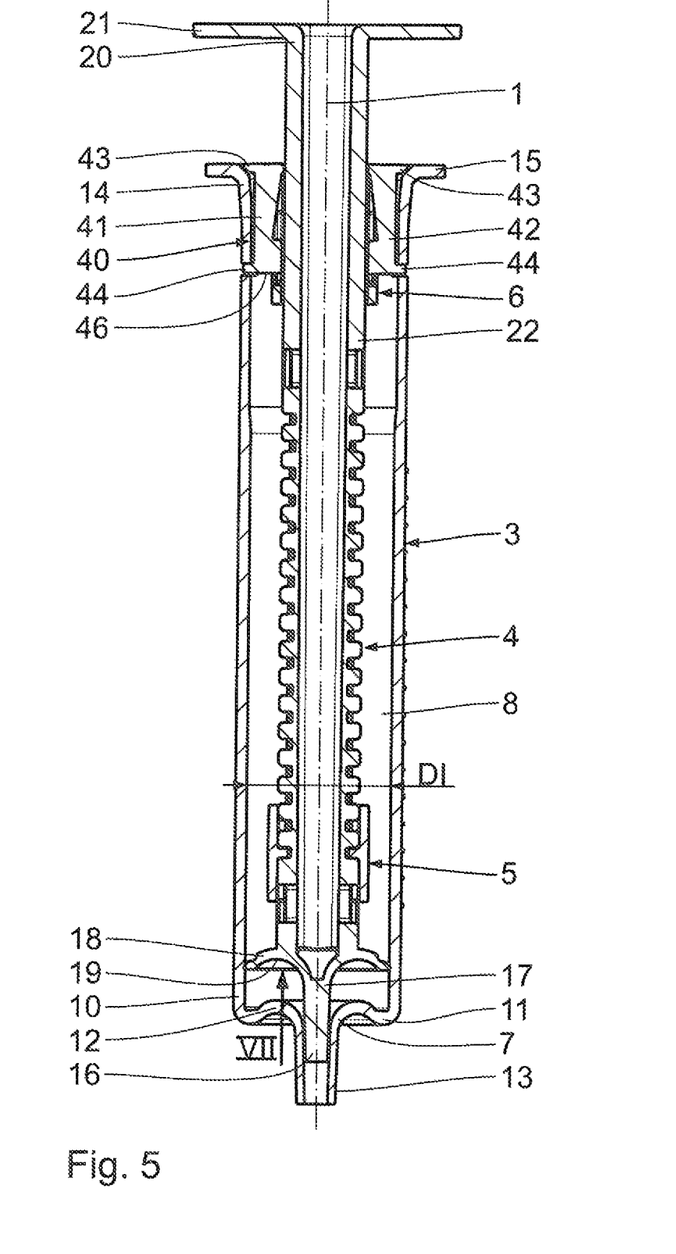
Figure 6:
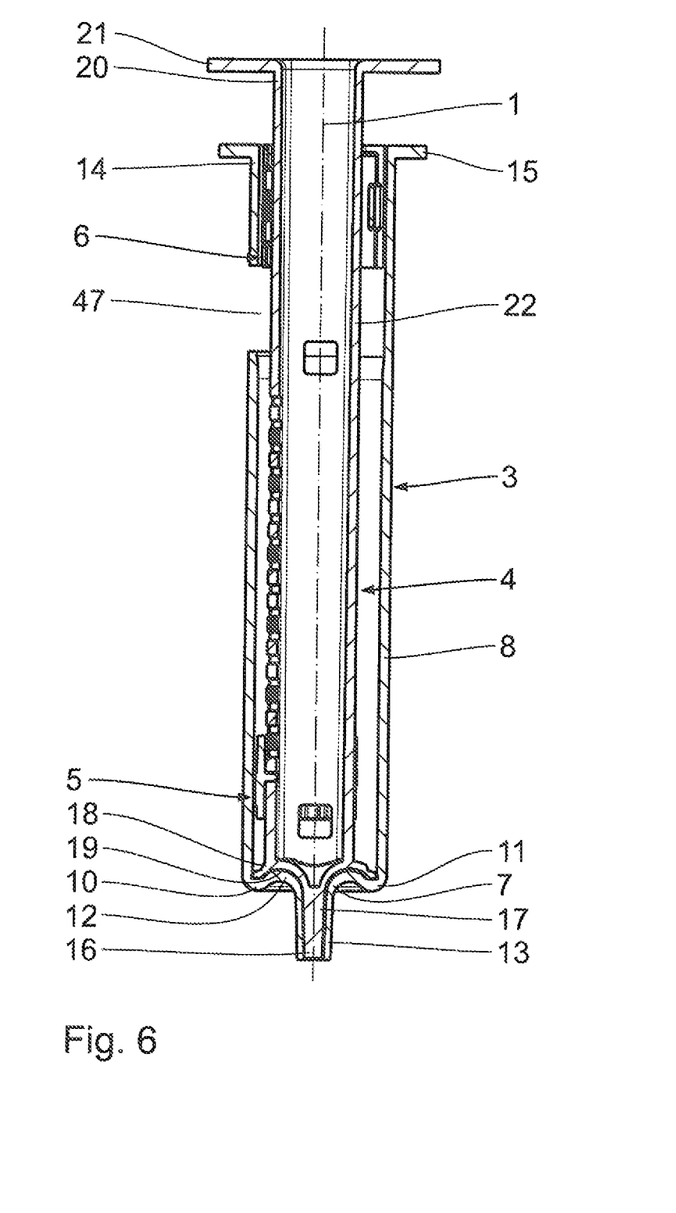
Figure 7:
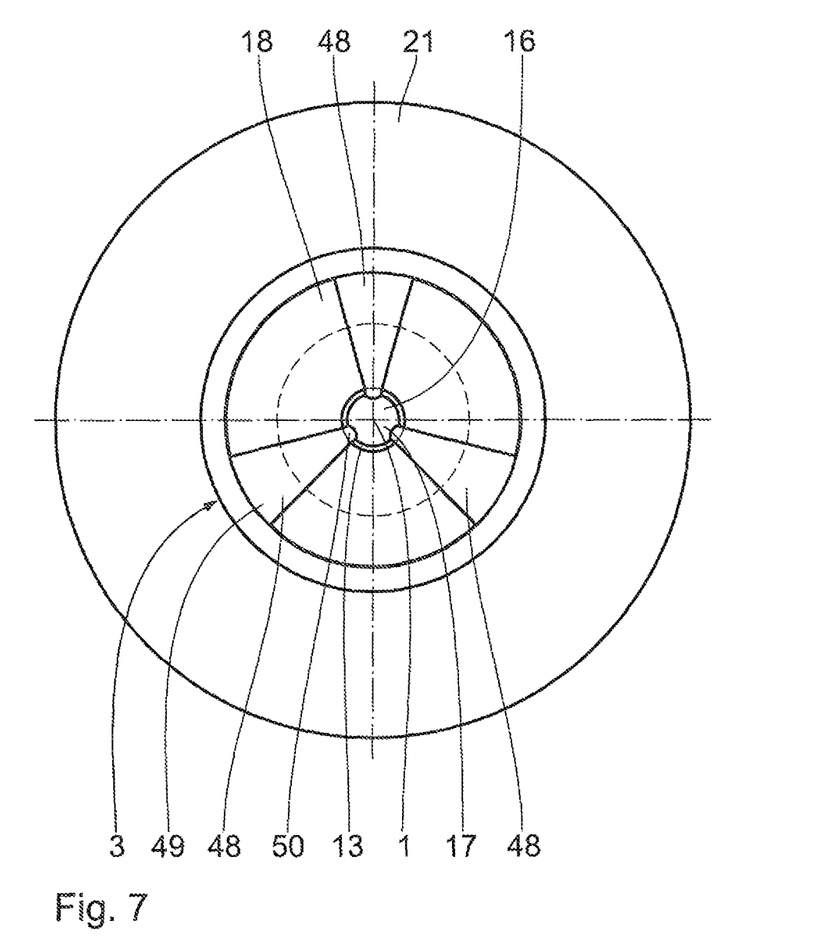

A dosing system as represented in FIGS. 1 to 6 has a longitudinal center axis 1 and is symmetrical in design with respect to a plane of symmetry 2. The longitudinal center axis 1 lies in the plane of symmetry 2.

The dosing system comprises a dosing sleeve 3 and a dosing plunger 4 movably guided in the dosing sleeve 3 relative to it in the direction of the longitudinal center axis 1. The dosing plunger 4 can move between a retracted position and a depressed position axially with respect to the dosing sleeve 3. The dosing system moreover has a retraction limiting element 5, which is axially fixable on the dosing plunger 4 in various positions which are spaced apart from each other in the direction of the longitudinal center axis 1 and thus locally delimits the maximum retraction path of the dosing plunger 4. An end stop 6 is arranged on the dosing sleeve 3 for mechanical interaction with the retraction limiting element 5 in the retracted position. The dosing sleeve 3 has a communication opening 7 for communicating with the outside. This delimits a storage space 8 for a fluid medium (not shown).

Depending on the local axial fixation of the retraction limiting element 5 with respect to the dosing plunger 4, the maximum retraction path of the dosing plunger 4 or the maximum dose volume can be adjusted individually. The maximum retraction path is limited by the end stop 6 and the retraction limiting element 5.

When the dosing plunger 4 is switched axially from its depressed position to a retracted position, a liquid medium can be drawn through the communication opening 7 into the storage space 8. On the other hand, when the dosing plunger 4 is moved axially from a retracted position to its depressed position, the medium located in the storage space 8 can be dispensed or squirted out through the communication opening 7. In the retracted position, the dosing plunger 4 is at least partly pulled out from the dosing sleeve 3, while in the depressed position the dosing plunger 4 is entirely shoved into the dosing sleeve 3.

The dosing sleeve 3 is formed from plastic, which is preferably transparent. It has a dosage scale 9. The dosing sleeve 3 is configured as a cylinder body, basically having a constant interior diameter DI in the direction of the longitudinal center axis 1 and being closed at a first end 10 by a dosing sleeve bottom 11. The dosing sleeve bottom 11 has here an annular bulge 12 projecting inward into the storage space 8, running about the longitudinal center axis 1. The communication opening 7 is arranged centrally in the dosing sleeve bottom 11. The dosing sleeve bottom 11 in the region of the communication opening 7 adjoins a tube piece 13 on the outside, whose internal diameter is much smaller than the internal diameter DI of the dosing sleeve 3.

The dosing sleeve 3 furthermore has a second end 14, which is opposite the first end 10. In the area of the second end 14, a circumferential flange 15 projects radially outward, forming a handle.

The dosing plunger 4 is likewise made of plastic. It has at its first end 16 a displacement body or ejection body 17 projecting in the direction of the longitudinal center axis 1, whose outer diameter basically corresponds to the interior diameter of the tube piece 13. The axial length of the displacement body 17 basically corresponds to the axial length of the tube piece 13. The displacement body 17 is essentially cylindrical in configuration and thus has a closed, circular cross section.

Adjoining the displacement body 17 is a radially projecting piston bottom 18, which is part of the dosing plunger 4 and has an outer diameter that essentially corresponds to the inner diameter DI of the dosing sleeve 3. The piston bottom 18 lies tight at its edges on the inside against the dosing sleeve 3. In the piston bottom 18 there is provided an annular depression 19 on the side facing the dosing sleeve bottom 11, which extends about the longitudinal center axis 1 and is complementary in configuration to the bulge 12.

The dosing plunger 4 has three drainage grooves 48 arranged at a spacing from each other, extending in the piston bottom 18 at the side facing the dosing sleeve bottom 11 and in the displacement body 17. Each drainage groove 48 thus has a drainage groove bottom section 49 in the piston bottom 18 and directly adjoining this a drainage groove displacement body section 50 in the displacement body 17, which stand in direct drainage or flow connection with each other.

The drainage groove bottom sections 49 each emerge from the outer edge of the piston bottom 18 and run from here radially inward in the direction of the longitudinal center axis 1 as far as the displacement body 17. In this, they taper continuously.

The drainage groove displacement body sections 50, which stand in a drainage or flow connection with the respective drainage groove bottom sections 49, extend in the displacement body 17 from a region immediately adjacent to the piston bottom 18 as far as its free end. They each have essentially constant width and extend essentially parallel to the longitudinal center axis 1.

Each drainage groove 48 lies in a plane that also encloses the longitudinal center axis 1. A different number of drainage grooves 48 is alternatively possible. The drainage grooves 48 are independent, of each other.

Opposite the first end 16, the dosing plunger 4 has a second end 20, on which a radially outwardly projecting activation shoulder 21 is arranged.

Between the piston bottom 18 and the second activation shoulder 21, the dosing plunger 4 has a shaft region 22. In the shaft region 22, the dosing plunger 4 essentially has a rectangular cross section. The dosing plunger 4 here is essentially configured as a profiled rectangular body. It has two opposite side walls 23 in the shaft region 22, which run parallel to each other and are joined to each other by an inner wall 24 and a front wall 25. The side walls 23 extend parallel to the plane of symmetry 2, while the inner wall 24 and the front wall 25 run basically perpendicular to this. The transverse dimension of the dosing plunger 4 in its shaft region 22 is smaller than the inner diameter DI of the dosing sleeve 3.

The front wall 25 projects laterally with respect to the side walls 23, forming rear retaining shoulders 26. Furthermore, it is slightly outwardly curved between the side walls 23.

In each side wall 23 there are arranged here a plurality of first and second locking elements 27 and 28 on the outside, being configured as locking element seats and being open at the side. The first and second locking element seats 27, 28 are each separately configured and arranged at a spacing from each other perpendicular to the longitudinal center axis 1. The first locking element seats 27 arranged in the side walls 23 lie opposite each other and have an identical distance from the front wall 25. The second locking element seats 28 arranged in the side walls 23 again lie opposite each other and have an identical distance from the front wall 25. The first locking element seats 27 are arranged further from the front wall 25 than the second locking element seats 28. A different number of locking element seats 27, 28 arranged one behind the other in relation to the front wall 25 is alternatively possible.

The first locking element seats 27 arranged in the side walls 23 are arranged at a spacing from each other in a first row in the direction of the longitudinal center axis 1. The second locking element seats 28 arranged in the side walls 23 are spaced apart from each other in a second row in the direction of the longitudinal center axis 1. The first and second locking element seats 27 and 28 are shown here as depressions. A different configuration is alternatively possible.

Moreover, in the middle of the front wall 25 there is arranged a plurality of separate form-fitting seats 29 on the outside and in front. The form-fitting seats 29 in the front wall 25 are also spaced apart in a row in the direction of the longitudinal center axis 1. The form-fitting seats 29, however, are configured as openings, preferably' having an elongated rectangular shape and running parallel to each other.

It is advantageous for the mutually opposite first and second locking element seats 27 and 28 and an adjacent form-fitting seat 29 to lie in a common plane each time.

Advisedly, the first and second locking element seats 27, 28 and the form-fitting seat 29 are provided, over a region on the dosing plunger 4 that extends for at least 30% of the overall length of the dosing plunger 4.

In each side wall 23 there are provided several feedback recesses or interruptions 51, each of them being arranged at a spacing from each other in the direction of the longitudinal center axis 1 and extending over the entire width of the particular side wall 23. The feedback recesses 51 each time extend essentially perpendicularly between the inner wall 24 and the front wall 25.

The retraction limiting element 5 is made of plastic. It has the configuration of a clamp with two opposite U legs 30 running essentially parallel to each other and joined by a U bottom 31. It is advantageous for the U legs 30 to be able to spring together and away from each other.

The U bottom 31 has an outwardly facing outside 32, whose curvature is adapted to the interior curvature of the dosing sleeve 3. Opposite to the outside 32, the U bottom 31 has an inside 33, whose curvature is adapted to the curvature of the front wall 25. From the inside 33 in the middle there is an inwardly projecting perpendicular form fitting means 34 in the form of a shoulder. The cross section of the form fitting means 34 is adapted to the cross section of the form-fitting seats 29. It is advantageous for the form fitting means 34 to taper from the inside 33 of the U bottom 31.

Adjacent to the U bottom 31 there is arranged on the inside of the two U legs 30 a retaining projection 35 with a corresponding retaining surface 36 facing the U bottom 31.

Opposite to the U bottom 31 each U leg 30 has an inner end 37. On the inside of each U leg 30 in the area of the inner end 37 there is arranged a first projecting locking abutment 38. The first locking abutments 38 emerge from the U legs 30 toward each other. The first locking abutments 38 are adapted in their shape to the first locking element seats 27.

Moreover, on each U leg 30 there is arranged on the inside a second projecting locking abutment 39, which is arranged between the U bottom 31 and the first locking abutment 38. The second locking abutments 39 emerge from the U legs 30 toward each other. They are adapted in their shape to the second locking element seats 28.

The mutual spacing between the first and second locking abutments 38 and 39 on a U leg 30 essentially corresponds to the spacing of the first and second locking element seats 27 and 28 on a side wall 23. It is advantageous for the first and second locking abutments 38 and 39 and the form fitting means 34 to lie in a common plane. An offset arrangement is alternatively possible.

The retraction limiting element 5 is smaller in its transverse dimensions perpendicular to the longitudinal center axis 1 than the inner diameter DI of the dosing sleeve 3. This pertains to both width and depth. The retraction limiting element 5 can thus be accommodated in the dosing sleeve 3.

In the area of the second end 14, a closure body 40 is inserted into the dosing sleeve 3, being configured as a bushing. The closure body 40 is formed by two closure body halves 41, 42, which are joined together by a hinge, preferably a film hinge. The hinge axis extends parallel to the longitudinal center axis 1. The dosing plunger 4 passes through the closure body 40 by its shaft region 22.

Opposite to the hinge, a locking lug is arranged on one closure body half 41, which engages in the folded state of the closure body halves 41, 42 with a locking recess on the other closure body half 42 and thus secures the closure body halves 41, 42 to each other in the folded state.

On the outside top of the closure body halves 41, 42 there is provided a radially projecting bearing shoulder 43, which lies against the dosing sleeve 3 in the region of the circumferential flange 15 at the top. Moreover, each closure body half 41, 42 has at the bottom a radially projecting locking body 44, which engages on the inside in a correspondingly dimensioned and situated locking recess 45 on the dosing sleeve 3. Thanks to the bearing shoulders 43 and the locking bodies 44, the closure body 40 is axially and angularly fixed to the dosing sleeve 3 and delimits it.

Alternatively, in the region of the second end 14, the closure body 40 having the shape of a bushing, for example, is screwed, glued, inserted or the like into the dosing sleeve 3. The closure body 40 is then configured appropriately.

In one variant of the dosing system not shown, the closure body 40 is not configured as a separate part. A part taking over the function of the closure body can be integrated as a structural element in a region of the dosing plunger 4, separated by film hinges for example. When assembling the dosing system, these structural elements can then act as an end stop for the retraction limiting element 5, for example, by folding them over.

The closure body 40 furthermore has an inner bottom surface 46, oriented perpendicular to the longitudinal center axis 1, from which the end stop 6 projects downward in the direction of the longitudinal center axis 1 toward the dosing sleeve bottom 11. The end stop 6 is essentially in the shape of a ring and it extends around the longitudinal center axis 1. It encircles the dosing plunger 4 or its shaft region 22.

In the region of the end stop 6, an activation window 47 is arranged in the dosing sleeve 3, which extends across a circumferential region of the dosing sleeve 3 and affords access from the outside to the storage space 8. The activation window 47 has a dimension in the direction of the longitudinal center axis 1 that essentially corresponds to the dimension of the retraction limiting element 5 in the direction of the longitudinal center axis 1. Moreover, the activation window 47 has a width perpendicular to the longitudinal center axis 1 that is broader than the width of the retraction limiting element 5 in the region of the U bottom 31 perpendicular to the longitudinal center axis 1.

The dosing system shall now be described more closely in use. We shall begin with the position indicated in FIG. 1. The piston bottom 18 here is arranged at a spacing from the dosing sleeve bottom 11. The dosing plunger 4 is situated in a retracted position. The retraction limiting element 5 is in its radially outer position, so that the U bottom 31 of the retraction limiting element 5 passes through the activation window 47 from the inside to the outside like a bar and is thus arranged adjacent to the walls of the dosing sleeve 3 bounding the activation window 47. The U bottom 31 is arranged at a spacing from the front wall 25. The first and second locking abutments 38 and 39 are disengaged from the first and second locking element seats 27 and 28. The form fitting means 34 on the retraction limiting element 5 moreover is disengaged from the form-fitting seats 29. The dosing plunger 4 can be moved with respect to the dosing sleeve 3 or the retraction limiting element 5 in the direction of the longitudinal center axis 1. The retaining surfaces 36 of the retraction limiting element 5 lie on the inside against the retaining shoulders 26 of the dosing plunger 4, so that a further radial pulling out of the retraction limiting element 5 is prevented.

The dosing plunger 4 is now manually moved into its desired dose setting along the longitudinal center axis 1. A corresponding force can be exerted in this way between the activation shoulder 21 and the circumferential flange 15. There follows a relative axial movement between the dosing plunger 4 and the dosing sleeve 3 and the retraction limiting element 5. An acoustic and tactile feedback is given to the user, due to the temporary engaging of the first and second locking abutments 38, 39 in the feedback recesses 51. When the desired dose setting of the dosing plunger 4 relative to the dosing sleeve 3 is reached, the retraction limiting element 5 is pressed via its activation knob in the radial direction from its outer position to its inner position, wherein preferably a frictional force must be overcome between the retraction limiting element 5 and the dosing plunger 4 and/or the dosing sleeve 3. During the radial movement of the retraction limiting element 5 inward, the form fitting means 34 is moved forward into the neighboring form-fitting seat 29, while the first and second locking abutments 38 and 39 lock sideways into the adjacent first and second locking element seats 27 and 28 and thus secure the retraction limiting element 5 axially and radially inseparably to the dosing plunger 4. The U bottom 31 is now also entirely inside the dosing sleeve 3 or in its storage space 8. It is now arranged at a spacing on the inside from the walls of the dosing sleeve 3 bounding the activation window 47. The U bottom 31 on the outside lies against the front wall 25.

The dosing plunger 4 can now be retracted until the retraction limiting element 5 strikes against the end stop 6 at the top. When the dosing plunger 4 is pushed into its depressed position, the medium located in the storage space 8 is ejected through the communication opening 7. During the movement of the dosing plunger 4, the retraction limiting element 5 moves along with the dosing plunger 4. The outside 32 in the inner position of the retraction limiting element 5 inside the dosing sleeve 3 moves axially with respect to this. The inner ends 37 in the inner position of the retraction limiting element 5 are still arranged at a spacing from the inside of the dosing sleeve 3.

In the fully depressed position, the bulge 12 engages with the depression 19, so that an especially good emptying of the medium situated in the storage space 8 is possible. The displacement body 17 engages in the tube piece 13 and forces out the medium situated herein through the tube piece 13. Thus, the displacement body 17 acts as an additional displacing part, so that the medium being dispensed can be dispensed essentially with no portion remaining in the space 8. The medium being dispensed goes through the drainage groove(s) 48 out from the storage space 8 when the displacement body 17 engages in the tube piece 13. The drainage groove(s) 48 facilitate the emptying of the remainder.

The invention claimed is:
1. A dosing system for adjusting a dose volume of a fluid medium, comprising:
   a) a longitudinal center axis, b) a dosing sleeve with at least one communication opening for communicating with the surroundings, c) a dosing plunger, which is displaceable in the dosing sleeve in the direction of the longitudinal center axis between a retracted position and a depressed position in order to take up and dispense the medium through the at least one communication opening, d) a retraction limiting element to delimit a maximum retraction path of the dosing plunger in the direction of the longitudinal center axis,
  i) wherein the retraction limiting element is axially fixable in at least one position to the dosing plunger,
  ii) wherein the retraction limiting element is radially displaceable to the longitudinal center axis between a radially inner position, axially fixed to the dosing plunger, and a radially outer position in regard to the dosing plunger, and
  iii) wherein the retraction limiting element in the inner position is entirely arranged inside the dosing sleeve, and e) an end stop arranged on the dosing sleeve for interacting with the retraction limiting element in the retracted position of the dosing plunger.

2. The dosing system according to claim 1, wherein a maximum dimension of the retraction limiting element perpendicular to the longitudinal center axis is smaller than an inner diameter of the dosing sleeve.

3. The dosing system according to claim 1, wherein the retraction limiting element in the inner position is locally axially fixed by a form-fitting connection to the dosing plunger.

4. The dosing system according to claim 3, wherein several first form-fitting means are provided on the dosing plunger, being arranged at a spacing from each other in the direction of the longitudinal center axis, while at least one second form-fitting means is provided on the retraction limiting element for the form-fitting interaction with at least one of the first form-fitting means.

5. The dosing system according to claim 1, wherein the retraction limiting element in the inner position is inseparably locally fixed to the dosing plunger.

6. The dosing system according to claim 1, wherein the retraction limiting element situated in the outer position interacts with the dosing plunger upon axial displacement of the dosing plunger in order to give a feedback in regard to the at least one position for the axial fixation of the retraction limiting element to the dosing plunger.

7. The dosing system according to claim 1, wherein an activation window for the retraction limiting element is formed in a side of the dosing sleeve.

8. The dosing system according to claim 7, wherein the retraction limiting element in the outer position passes through the activation window like a bar and is substantially flush on the outside with the dosing sleeve.

9. The dosing system according to claim 7, wherein the retraction limiting element has a dimension in the direction of the longitudinal center axis that substantially corresponds to the dimension of the activation window in the direction of the longitudinal center axis.

10. The dosing system according to claim 7, wherein the retraction limiting element has a width perpendicular to the longitudinal center axis which substantially corresponds to a width of the activation window disposed perpendicular to the longitudinal center axis.

11. The dosing system according to claim 8, wherein the activation window is arranged adjacent to the end stop and in front of the end stop in the retraction direction of the dosing plunger.

12. The dosing system according to claim 1, wherein the end stop is formed separate from the dosing sleeve and is secured by a locking connection to the dosing sleeve.

13. The dosing system according to claim 1, wherein the end stop is arranged adjacent to a second end of the dosing sleeve located opposite to the at least one communication opening.

14. The dosing system according to claim 1, wherein the dosing plunger is axially movable relative to the retraction limiting element when the retraction limiting element is in the outer position.

15. The dosing system according to claim 1, further comprising a retaining mechanism disposed between the dosing plunger and the retraction limiting element which limits the outward radial displacement of the retraction limiting element.

16. A dosing system for adjusting a dose volume of a fluid medium, comprising:

a) an elongate generally cylindrical dosing sleeve having an opening at one end through which the medium is dispensed;

b) a plunger telescopically received in the dosing sleeve that is movable relative to the dosing sleeve to take up and dispense the medium through the opening in the dosing sleeve, the plunger movable relative to the dosing sleeve between a fully retracted position and a fully depressed position; and c) a retraction limiting element radially movable relative to the plunger between (i) a dosing setting adjustment position where the plunger is movable axially relative to the retraction limiting element enabling adjustment of the dose volume between one of a plurality of dose volumes, and (ii) a dose setting position where the retraction limiting element is releasably fixed to the plunger at one of a plurality of axial locations along the plunger corresponding to a desired dose setting such that the retraction limiting element moves within the dosing sleeve in unison with the plunger limiting retraction of the plunger within the dosing sleeve to take up the dose volume of the medium corresponding to the desired dose setting; and wherein the dosing sleeve further comprises an end stop against which the retracting limiting element abuts when the retracting limiting element is releasably fixed to the plunger and the plunger is retracted to a position that is less than the fully retracted position.

17. The dosing system according to claim 16, wherein the retraction limiting element (i) engages the plunger in a manner permitting relative movement therebetween when disposed in the dosing setting adjustment position, and (ii) is moved radially relative to the plunger from the dosing setting adjustment position toward the plunger to the dose setting position releasably fixing the retraction limiting element to the plunger for movement in unison therewith.

18. The dosing system according to claim 16, wherein the dosing sleeve has a window formed therein through which the retraction limiting element is inserted and manipulated into engagement with the plunger.

19. A dosing system for adjusting a dose volume of a fluid medium, comprising:

a) an elongate generally cylindrical dosing sleeve having an opening at one end through which the medium is dispensed;

b) a plunger telescopically received in the dosing sleeve that is movable relative to the dosing sleeve to take up and dispense the medium through the opening in the dosing sleeve, the plunger movable relative to the dosing sleeve between a fully retracted position and a fully depressed position; and c) a retraction limiting element radially movable relative to the plunger between (i) a dosing setting adjustment position where the plunger is movable axially relative to the retraction limiting element enabling adjustment of a dose volume between one of a plurality of dose volumes, and (ii) a dose setting position where the retraction limiting element is releasably fixed to the plunger at one of a plurality of axial locations along the plunger corresponding to a desired dose setting such that the retraction limiting element moves within the dosing sleeve in unison with the plunger limiting retraction of the plunger within the dosing sleeve to take up the dose volume of the medium corresponding to the desired dose setting; and wherein the retraction limiting element comprises a generally U-shaped clamp having a pair of legs straddling the plunger.

20. The dosing system according to claim 19, wherein the dosing sleeve further comprises an end stop against which the retracting limiting element abuts when the retracting limiting element is releasably fixed to the plunger and the plunger is retracted to a position that is less than the fully retracted position.

* * * * *